United States Patent [19]
Hutchinson et al.

[11] Patent Number: 5,889,023
[45] Date of Patent: Mar. 30, 1999

[54] FIBRINOGEN RECEPTOR ANTAGONIST

[75] Inventors: John H. Hutchinson, Philadelphia; George D. Hartman; Wasyl Halczenko, both of Lansdale, all of Pa.

[73] Assignee: Merck & Co., Inc., Rahway, N.J.

[21] Appl. No.: 841,884

[22] Filed: May 5, 1997

Related U.S. Application Data

[60] Provisional application No. 60/017,557 May 10, 1996.

[51] Int. Cl.$^6$ ........................ A61K 31/445; C07D 401/14
[52] U.S. Cl. ............................................. 514/318; 546/187
[58] Field of Search ............................... 546/187; 514/318

[56] References Cited

U.S. PATENT DOCUMENTS

| | | | |
|---|---|---|---|
| 4,064,255 | 12/1977 | Cahmpseix et al. | 424/267 |
| 4,122,255 | 10/1978 | Krapcho | 542/421 |
| 4,243,807 | 1/1981 | Friebe et al. | 546/232 |
| 4,622,331 | 11/1986 | Jozic | 514/331 |
| 5,030,654 | 7/1991 | Barnish et al. | 514/510 |
| 5,064,814 | 11/1991 | Klein et al. | 514/18 |
| 5,281,585 | 1/1994 | Duggan et al. | 514/79 |
| 5,665,882 | 9/1997 | Chung | 546/193 |

FOREIGN PATENT DOCUMENTS

| | | |
|---|---|---|
| 0 352 249 | 1/1990 | European Pat. Off. . |
| 0 372 486 | 6/1990 | European Pat. Off. . |
| 0 381 033 | 8/1990 | European Pat. Off. . |
| 0 384 362 | 8/1990 | European Pat. Off. . |
| 0 405 537 | 1/1991 | European Pat. Off. . |
| 0 478 328 | 4/1992 | European Pat. Off. . |
| 0 478 362 | 4/1992 | European Pat. Off. . |
| 97/14417 | 4/1997 | WIPO . |

*Primary Examiner*—Evelyn Mei Huang
*Attorney, Agent, or Firm*—Richard S. Parr; Melvin Winokur

[57] ABSTRACT

A fibrinogen receptor antagonist which is 3(R)-[2-(Piperidin-4-yl)ethyl]-2-piperidon-1-ylacetyl-3(S)-(3-pyridyl)-β-alanine.

5 Claims, No Drawings

FIBRINOGEN RECEPTOR ANTAGONIST

This application claims the benefit of provisional application 60/017,557 filed on May 10, 1996.

BACKGROUND OF THE INVENTION

The invention relates generally to modulating cell adhesion and to inhibiting the binding of fibrinogen and other proteins to blood platelets, and inhibiting the aggregation of blood platelets specifically to the gp IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothethial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in *Science*, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in *Proc. Nat'l Acad. Sci. U.S.A.*, 84, 6471–6475, (1987), describes an Arg-Gly-Asp directed adhesion receptor expressed by human endothethial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in *J. of Biol. Chem.*, 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the sterochemical conformation of Arg-Gly-Asp as influenced by enantiomeric substitutions or additions to this sequence significantly influenced receptor-ligand interaction. The authors further showed that cyclization of a decapeptide by forming a disulfide bridge between non-terminal residues Pen and Cys, rendered the peptide much less effective at inhibiting attachment to fibronectin.

In *Proc. Nat'l Acad. Sci. U.S.A.*, 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and U.S. Pat. No. 4,578,079.

Ruggeri et al., *Proc. Nat'l Acad. Sci. U.S.A.*, 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., *biochem.* 23, 1767–1774 (1984); Ginsberg et al., *J. Biol. Chem.* 260(7), 3931–3936 (1985); and Haverstick et al., *Blood* 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gp IIb/IIIa complex. For example, Huang et al., *J. Biol Chem.*, 262, 16157–16163 (1987); Huang et al., *Biochemistry*, 28, 661–666 (1989) describe the primary structure of the venom trigramin which is a 72 amino acid polypeptide that contains the RGD subunit. Echistatin is another compound which has high affinity for the gp IIb/IIIa complex. This polypeptide contains 49 amino acids and has the RGD subunit and various disulfide bridges. Gan et al., *J. Biol. Chem.*, 263, 19827–19832 (1988). See also, Dennis et al., *Proc. Nat'l Acad. Sci. USA*, 87, 2471–2475 (1989). However, these snake venom factors also have high affinity for other members of the adhesive protein receptor family including the vitronectin and fibronectin receptors so are not selective for the gp IIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No. 5,023,233, assigned to Merck & Co., Inc., discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gp IIb/IIIa receptor. U.S. Pat. No. 5,037,808 discloses guanidino peptide mimetic compounds that retain an Asp residue which inhibit platelet aggregation. WO 9014103 describes the use of antibody-poly-peptide conjugates wherein said polypeptides contain the Arg-Gly-Asp (RGD) sequence.

WO 9111458 discloses the use of large cyclic peptides containing RGD flanked by proline residues which are platelet aggregation inhibitors. WO 9101331 discloses small cyclic platelet aggregation inhibitors which are synthetic cyclic pentapeptides containing the tripeptide sequence Arg-Gly-Asp and a thioether linkage in the cycle. Hartman et al., WO 9408962 discloses compounds which are effective for inhibiting platelet aggregation by inhibiting fibrinogen binding to the gp IIb/IIIa receptor site, e.g., 5-[2-(4-piperidinyl) ethyl oxyl]-2-indolecarbonyl-2(S)-phenylsulfonylamino-β-alanine (compound II, FIG. 1B), and related compounds. U.S. Pat. No. 5,051,405 discloses the use of peptides and pseudopeptides such as N-amidino piperidine-3-carboxylglycyl-L-aspartyl-L-valine that inhibit platelet aggregation and thrombus formation in mammalian blood. EP 445 796 discloses linear compounds which can include internal piperazinyl or piperidinyl derivatives. EP 437 367 discloses linear polypeptide fibrinogen receptor antagonists.

U.S. Pat. No. 5,265,812 discloses compounds of the structure $R^1$-A-(W)a-X-($CH_2$)b-(Y)$_c$-B-Z-COOR wherein $R^1$ is a guanidino or amidino moiety and A and B are chosen from specific monosubstituted aryl or heterocyclic moieties.

U.S. Pat. No. 5,281,585 describes a series of 1,3 disubstituted piperidones which are useful as oral fibrinogen receptor antagonists. One such compound, 3(R)-[2-Piperidin-4-yl ethyl[-2-piperidone-1]acetyl-3(R)-methyl-β-alanine; is specifically described on column 15, line 8, columns 35–40, and columns 63–67. The compound is one of the most potent of these piperidones, having an $IC_{50}$ for inhibiting aggregation of about 30 nm. Following administration of 0.3 mg/kg, p.o. to the compound inhibited platelet aggregation between 90–100% during the first three hours. Inhibition decreased over time, dropping below 20% after 8 hours.

The present invention provides a novel fibrinogen receptor antagonist that has significant, extended oral activity and is, therefore, useful for the reasons stated herein. The antagonist inhibits platelet aggregation at about 100% over an entire 8 hour period. A number of serious diseases and disorders involve hyperthrombotic complications which lead to intravascular thrombi and emboli. Myocardial infarction, stroke, phlebitis and a number of other serious conditions create the need for a fibrinogen receptor antagonist having potent and long-lasting efficacy.

SUMMARY OF THE INVENTION

The invention is the fibrinogen receptor antagonist 3(R)-[2-(Piperidin-4-yl)ethyl]-2-piperidon-1-ylacetyl-3(S)-(3-pyridyl)-β-alanine and pharmaceutically acceptable salts, racemates and racemic mixtures thereof, hydrates and polymorphs, hereinafter referred to as active drug.

Active drug of the invention is useful for inhibiting the binding of fibrinogen to blood platelets and for inhibiting the aggregation of blood platelets. The above-mentioned active drug can be used in a method of acting upon a fibrinogen receptor which comprises administering a therapeutically effective but non-toxic amount of such compound to a mammal, preferably a human. A pharmaceutical composition comprising a pharmaceutically acceptable carrier and, dispersed therein, an effective but non-toxic amount of active drug is another feature of this invention.

DETAILED DESCRIPTION OF THE INVENTION

The fibrinogen receptor antagonist compound of the present invention, 3(R)-[2-(Piperidin-4-yl)ethyl]-2-piperidon-1-ylacetyl-3(S)-(3-pyridyl)-β-alanine, and pharmaceutically acceptable salts thereof, racemates, racemic mixtures, hydrates and polymorphs, is useful as an orally active compound for inhibiting the binding of fibrinogen to blood platelets and for inhibiting the aggregation of blood platelets.

One test which is used to evaluate fibrinogen receptor antagonist activity is based on evaluation of inhibition of ADP-stimulated platelets. Aggregation requires that fibrinogen bind to and occupy the platelet fibrinogen receptor site. [rihibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets ($2\times10^8$ per ml), fibrinogen (100 micrograms per ml (ug/ml)), $Ca^2+$(1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

In the procedure for determining potency of fibrinogen receptor antagonist following oral administration to a patient, tested compound is orally administered to a dog. Blood samples are drawn at various intervals over an 8 hour period and subjected to the ADP-stimulated platelet aggregation assay.

The results clearly show that 3(R)-[2-(Piperidin-4-yl)ethyl]-2-piperidon-1-ylacetyl-3(S)-(3-pyridyl)-β-alanine provided nearly 100% inhibition of platelet aggregation during the entire 8 hour test period. In contrast, 3(R)-[2-Piperidin-4-yl ethyl]-2-piperidone-1]acetyl-3 (R)-methyl-β-alanine provided between 90–100% inhibition of platelet aggregation during the first three hours and steadily declining levels of inhibition thereafter, dropping below 20% after 8 hours.

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

3(R)-[2-(Piperidin-4-yl)ethyl]-2-piperidon-1-ylacetyl-3 (S)-(3-pyridyl)-β-alanine is a chiral compound. Included within the scope of the present invention are racemic mixtures and separated enantiomers of the compound. Furthermore, hydrates as well as anhydrous compositions and polymorphs of the general formula are within the present invention. Thus, the term "active drug" includes 3(R)-[2-(Piperidin-4-yl)ethyl]-2-piperidon-1-ylacetyl-3(S)-(3-pyridyl)-β-alanine and its salts, racemic mixtures or separated enantiomers, hydrates or anhydrous forms, polymorphs, and pharmaceutically acceptable salts.

Prodrugs, such as ester derivatives of active drug are compound derivatives which, when absorbed into the bloodstream of a warm-blooded animal, cleave in such a manner as to release the drug form and permit the drug to afford improved therapeutic efficacy.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

In the schemes and examples below, various reagent symbols have the following meanings:
BOC (or Boc): t-butyloxycarbonyl
Pd-C: Palladium on activated carbon catalyst
DMF: Dimethylformamide
DMSO: Dimethylsulfoxide
CBZ: Carbobenzyloxy
$CH_2Cl_2$: Methylene chloride
$CHCl_3$: chloroform
EtOH: ethanol
MeOH: methanol
EtOAc: ethyl acetate
HOAc: acetic acid
BOP: Benzotriazol-1-yloxytris(dimethylamino) phosphonium, hexafluorophosphate
EDC: 1-(3-Dimethylaminopropyl)-3-ethylcarbodiimide hydrochloride
Oxone: potassium peroxymonosulfate
LDA: Lithium diisopropylamide Active drug can be administered in such oral forms as tablets, capsules (each of which includes sustained release or timed release formulations), pills, powders, granules, elixirs, tinctures, suspensions, syrups, and emulsions. Likewise, it may be administered in intravenous (bolus or infusion), intraperitoneal, subcutaneous, or intramusculsar form, all using forms well known to those of ordinary skill in the pharmaceutical arts. An effective but non-toxic amount of active drug can be employed as an anti-aggregation agent.

Active drug may be administered to patients where prevention of thrombosis by inhibiting binding of fibrinogen to the platelet membrane glycoprotein complex IIb/IIIa receptor is desired. It is useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Active drug may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gp IIb/IIIa on the platelet membranes and fibrinogen adsorbed to the surface of the circuit. (Gluszko et al., *Amer. J. Physiol.*, 252(H), 615–621 (1987)). Platelets released from artificial surfaces show impaired hemostatic function. Active drug may be administered to prevent adhesion.

Other applications of active drug include prevention of platelet thrombosis, thromboembolism and reocclusion during and after thrombolytic therapy and prevention of platelet thrombosis, thromboembolism and reocclusion after angioplasty or coronary artery bypass procedures. It may also be used to prevent myocardial infarction.

The dosage regimen utilizing active drug is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of active drug when used for the indicated effects, will range between about 0.005 mg per kg of body weight per day (mg/kg/day) to about 50 mg/kg/day and preferably 0.005–20 mg/kg/day and most preferably 0.005–10 mg/kg/day. For example, a typical 90 kg patient would receive oral dosages ranging between about 0.45 mg/day and about 4.5 g/day, most preferably between about 1.0 mg/day and 1.0 g/day. Suitable pharmaceutical oral compositions such as tablets or capsules may contain 1–500 mg, for example, 1 mg, 10 mg, 100 mg, 200 mg and 500 mg. Intravenously, the most preferred doses will range from about 0.5 to about 5 mg/kg/minute during a constant rate infusion. Active drug may be administered in one or divided doses of two, three, or four times daily. Furthermore, active drug can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

In the methods of the present invention, the active drug can form the active ingredient, and is typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels.

Active drug can also be co-administered with the usual doses of suitable anticoagulation agents, such as heparin or warfarin (typically given in tablet doses between 1 and 20 mg daily during administration of the active drug), or thrombolytic agents such as tissue plasminogen activator (typically given in i.v. doses of between 20 and 150 mg over two hour period prior to or during administration of the active drug), to achieve beneficial effects in the treatment of various vascular pathologies. Such co-administration also includes administration if the active drug with doses of anticoagulant agents or thrombolyric agents less than the usual doses of those agents.

3(R)-[2-(Piperidin-4-yl)ethyl]-2-piperidon-1-ylacetyl-3 (S)-(3-pyridyl)-β-alanine was prepared according to the procedure of the following example. Those skilled in the art will readily understand that known variations of the conditions and processes of the following preparative procedures can be used to prepare this compound. All temperatures are degrees Celsius unless otherwise noted.

In general, 2-piperidone is reacted with ethyl bromoacetate to form the piperidone ester. The ester is reacted with 4-vinylpyridine to form the pyridine ethyl ester. The ethyl ester is reacted with ammonium hydroxide to form an ammonium salt which is then hydrogenated and esterified. The piperidinyl ring of the resulting ester is protected, and the ester is hydrolyzed. The resulting acid is reacted with ethyl 3-pyridyl-β-aminopropionate dihydrochloride and deprotected to form 2-(piperidin-4-yl)ethyl]-2-piperidon- 1 -ylacetyl-(3-pyridyl)-β-alanine.

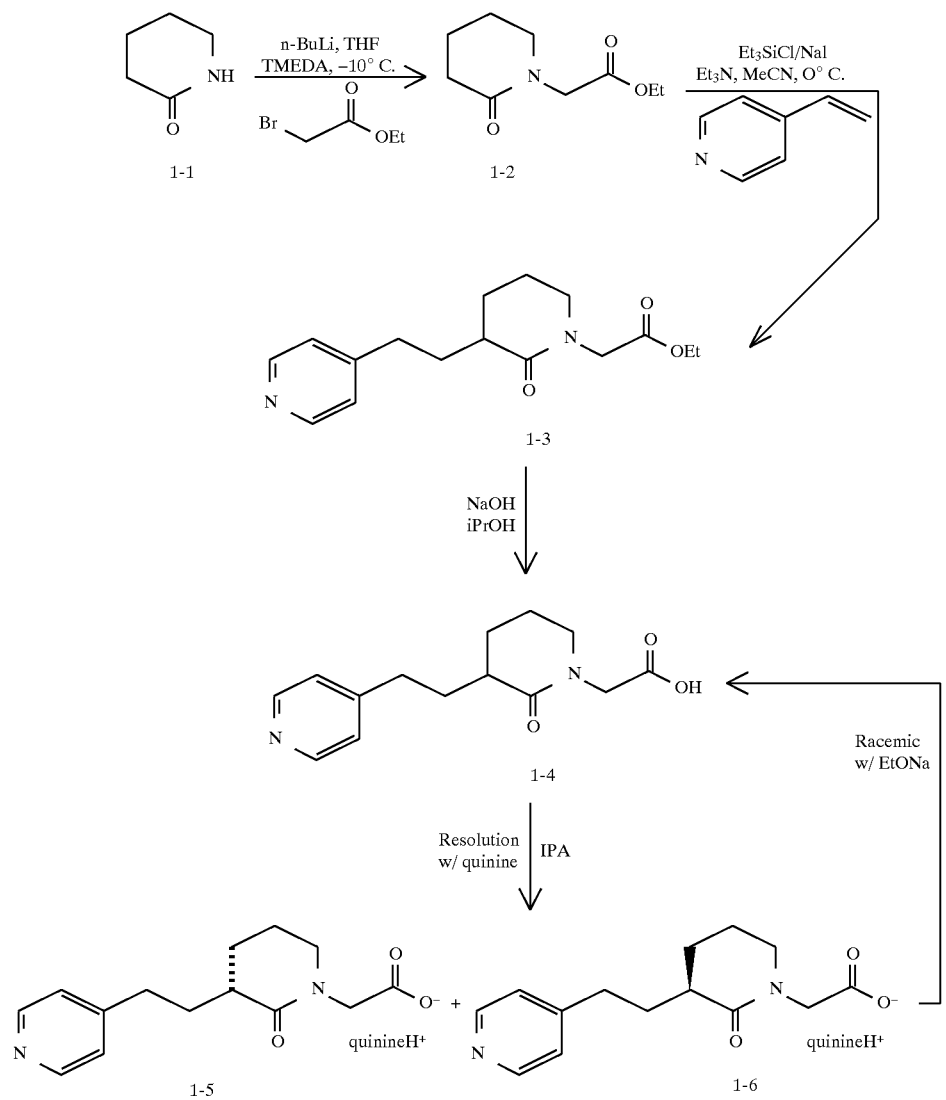

SCHEME 1

-continued
SCHEME 1

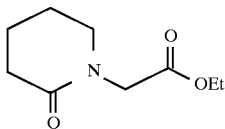

1-2

Ethyl (2-piperidon-1-yl]acetate (1-2)

A 5 L four-necked round bottom flask was charged with 2-piperidone 1-1 (160.00 g, 1.614 mol), THF (1.44 L) and TMEDA (206.3 g, 1.775 mol). The mixture was stirred until all the solid dissolved, then 3Å molecular sieves (26 g) were added. After stirring overnight, the mixture was filtered and the molecular sieves were washed with THF (0.48 L).

The combined filtrate was transferred to a dry 5 L four-necked round bottom flask equipped with a mechanical stirrer, an addition funnel, nitrogen inlet, cooling unit and a thermometer probe. The solution was cooled to −10° C. and n-butyllithium (1.6M in hexane, 1.06 L, 1.695 mol) was slowly added over a 60 min period, keeping the internal temperature less than 0° C. The mixture turned milky when ~50% of n-BuLi was charged. n-Butyllithium could be charged over 2–4 h while maintaining the internal temperature <5° C. without deterioration on the final yield. The only drawback was the slight increase in viscosity of the milky mixture.

After the addition, the reaction mixture was stirred at 0–5° C. for 1 h. The reaction mixture was cooled to −10° C., and ethyl bromoacetate (283.1 g, 1.695 mol) was added over 15 min while maintaining the internal temperature less than 0° C. Ethyl bromoacetate could be charged over 0.5–1 h while maintaining the internal temperature <20° C. without deterioration on the final yield. The reaction mixture was stirred at 0° C. for 15 min and then allowed to warm to 23° C. and aged at this temperature for a 2 h period (or overnight if needed).

The reaction mixture was cooled to between −5° and 0° C. and quenched into a solution of NaCl (170 g) in 2N HCl (1.78 L), keeping the internal temperature less than 20° C. The resulting aqueous phase had a pH of 6.

The mixture was transferred to a 12 L separatory funnel and the two layers were separated. The aqueous layer was extracted with i-propyl acetate (3×1 L).

The combined organic layers were concentrated to near dryness and then azeotropically dried with acetonitrile (3×600 mL) (50° C., house vacuum). The mixture was filtered to remove a small amount of NaCl after the azeotropic distillation. The filter cake was washed with 500 mL acetonitrile. The brown solution was used as is in the next step. Pure solid product 1-2 was isolated by crystallization from isopropyl acetate/hexane. mp: 70°–71° C.;

¹HNMR (CDCl₃, 250 MHz) δ: 1.27 (t, J=7.1 Hz, 3 H), 1.85 (br m, 4 H), 2.42 (br m, 2 H), 3.35 (br m, 2 H), 4.10 (s, 2 H), 4.19 (q, J=7.1 Hz, 2 H). ¹³C NMR (CDCl₃, 63 mHz) δ: 14.1, 21.3, 23.1, 32.1, 48.6, 49.2, 61.1, 169.1, 170.4.

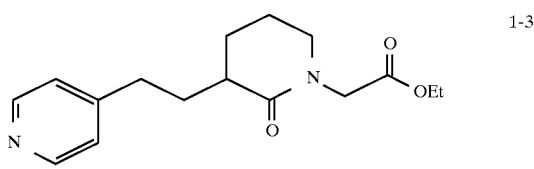

1-3

Ethyl [(±)3-[2-(pyridin-4-yl)ethyl]-2-piperidon-1-yl]acetate (1-3)

A 250 mL three-necked round bottom flask equipped with a stirrer, nitrogen inlet, cooling unit and a thermometer probe was charged with piperidone-ester 1-2 (55.6 g, 108.0 mmol; 36 wt %; from step 1), acetonitrile (63.0 mL), anhydrous sodium iodide (17.81 g, 118.8 mmol) and triethylamine (13.1 1 g, 129.6 mmol). The mixture was stirred until all the solid dissolved.

The solution was cooled to 0° C. and chlorotriethylsilane (17.91 g, 19.94 mmol) was added over 5 min, keeping the internal temperature below +5° C., and then stirred at 20° C. for 1–2 h.

The resulting mixture was cooled to −5° to 0° C., and 4-vinylpyridine (13.09 g, 124.2 mmol) was added dropwise over a 2 h period, while keeping the internal temperature below 0° C. The reaction was aged at 0° C. for 1–2 h, then quenched by slow addition (10 minutes) into a cold (0° C.) solution of 1N HCl (140 mL), while keeping the internal temperature <20° C. The final pH was 1.5–2.5.

The acidic solution (pH ~2) was extracted with 50% IPAC/Hexane (2×160 mL). Piperidone-ester 1-2 (5–7%), triethylsiloxane and residual neutral species were removed during the extractions.

To the aqueous solution was added IPAC (1×120 mL) and the mixture was cooled to 5°–10° C. With vigorous stirring, it was then basified to pH 9.5–10 by the slow addition of solid sodium bicarbonate (10 g; to pH 6) and 5N NaOH (~22 mL; to pH 9.7). The layers were separated.

The aqueous solution was extracted with toluene (2×150 mL). About 0. 1% product remained in the aqueous layer after the extractions.

The combined organic layers were washed with saturated aqueous sodium bicarbonate (3×50 mL). Three washes were required to remove 95+% of Et₃N.HI/NaI. Less than 0.5% of product was lost to the bicarbonate washes. The resulting organics has a total volume of 460 mL and a KF of 5.1 mg/mL.

The organic layer was azeotropically dried by distillation at 60° C. under reduce pressure. After 450 mL distilled out (final KF =<100 mg/mL), distillation was termninated and 150 mL dry toluene (total volume =200 mL) and 12 g of silica (60–200 mesh) were added. After stirring for 1 h, the mixture was filtered and the filter cake was washed with 100 mL toluene. Significant amounts of colored, polar, gummy impurities were removed by the silica treatment.

The combined filtrate was assayed to contain product 1-3. It was concentrated in vacuo (50° C., 100 mBar). After distilling most of the solvent, the batch was flushed with IPA (3×100 mL) to give a final concentration of 25 wt % (86 g) in IPA. This solution was used as is in the next step.

MS(EI) m/z 290 (M+). $^1$H NMR (CDCl$_3$) δ1.09 (t, J =7.1 Hz, 3H), 1.50 (m, 1H), 1.60–1.90 (m,2H), 2.04 (m, 1H), 2.20 (m, 1H), 2.54 (m, 2H), 3.10–3.30 (m, 2H), 3.77 (A of AB, J =17.2 Hz, 1H), 4.01 (q, J =7.1 Hz, 2H), 4.03 (B of AB, J=17.2 Hz, 1H), 6.99 (d, J =6.0 Hz, 2H), 8.30 (d, K =6.0 Hz, 2H). $^{13}$C NMR (CDCl$_3$) δ9.7, 17.3, 22.2, 27.9, 28.0, 36.2, 44.6, 44.9, 56.6, 119.5, 145.2, 146.6, 164.7, 168.2.

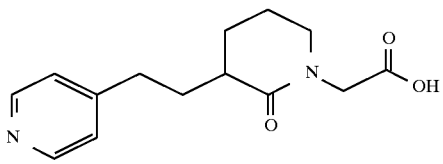

1-4

[(±)3-[2-(Pyridin-4-yl)ethyl]-2-piperidon-1-yl]acetic acid (1-4)

To a 25 wt % solution of the pyridine-ethyl ester 1-3 (21.3 g, 73.35 mmol) in isopropyl alcohol was added 48.8% aqueous sodium hydroxide (7.82 g, 95.36 mmol) at 20° C. under nitrogen over a 5 min period.

The reaction mixture was stirred for 2 h until complete consumption of 1-3 was observed as monitored by HPLC.

The mixture was cooled to 5°–10° C., seeded with 50 mg of NaCl and then quenched by the slow addition of 36.6% aqueous hydrochloric acid (9.50 g, 95.36 mmol) over a 10 min period, while maintaining the internal temperature <15° C. The final pH was 5.45.

To the resulting mixture was added MeOH (20 mL), THF (40 mL) and Solka-Floc (5 g). After stirring for 30 min at ambient temperature, the mixture was filtered through a pad of Solka-Floc (5 g, wetted with 10 mL EPA) in a 150 mL sintered glass funnel (10–15 mm).

The filter cake was washed with a mixture of IPA/THF/MeOH (50 mL:20 mL:10 mL). Filtration of the wash took about 3 min.

The combined filtrate contained acid 1-4 in quantitative yield as determined by HPLC analysis.

The filtrate was dried by azeotropic distillation under vacuum at 50° C. After distilling most of the solvents, the mixture was flushed several times with IPA (3×50 mL) to give a final concentration of 30 wt % (final weight =60 g) and a KF of <1000 mg/mL.

The mixture was seeded with 1-4 and stirred until a seed bed was formed. Hexane (20 g, 30.5 mL) was then added over a 1 h period and then aged for 12 h. After cooling to 10° C. and stirring for 0.5 h, the solid was collected by filtration through a sintered glass funnel. The filter cake was washed with 40:60 IPA:hexanes (50 mnL) and vacuum-dried under a stream of nitrogen to give 1-4 as a light beige crystalline solid. mp 144°–145° C.

MS(EI) m/z $_{263}$ (MH+). $^1$H NMR (CDCl$_3$) δ 1.70 (m, 1H), 1.80–2.05 (m, 4H), 2.20 (m, 1H), 2.40 (m, 1H), 2.78 (t, J =8.0 Hz, 2H), 3.35 (m, 1H), 3.47 (m, 1H), 3.90 (A of AB, J =17.1 Hz, 1H),4.32(B of AB, J=17.1 Hz, 1H),7.27 (d, J =6.2 Hz, 2H), 8.49 (d, J =6.0 Hz, 2H). $^{13}$C NMR (CDCl$_3$) δ 17.4, 22.4, 28.1, 28.4, 36.3, 44.9, 45.1, 120.4, 142.7, 149.8, 167.7, 168.3. Anal. Calcd for C$_{14}$H$_{18}$O$_3$N$_2$: C, 64.11; H, 6.92; N, 10.68. Found: C, 64.15; H, 7.16; N, 10.66.

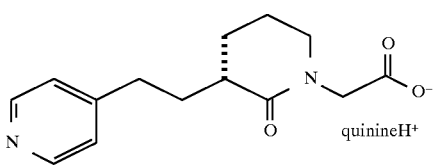

1-5

Quininium [3(R)-(−)-[2-(pyridin-4-yl)ethyl]-2-piperidon-1-yl]acetate (1-5) via resolution of [(+)3-[2-(pyridin-4-yl) ethyl]-2-piperidon-1-yl] acetic acid (1-4) with quinine In a 250 mL round bottom flask, pyridine acid 1-4 (12.04 g, 96.6% pure, 44.34 mmol), quinine (14.89 g, 45.90 mmol) and isopropyl alcohol (80.8 mL; KF <0. 1 mg/iL) were combined. The mixture was heated at 65° C. for 15 min under a nitrogen atmosphere to dissolve all the solid. The resulting solution was allowed to cool to 20° C. When the solution reached 45° C, it was seeded with ~10 mg of 99.5% ee quinine salt 1-5. After stirring overnight, the mixture was cooled to 5°–6° C. and aged for 0.5–1 h.

The solid was collected on a medium porosity fritted funnel under a nitrogen blanket. The filter cake was washed with 50 mL cold (5°–10° C.) THF:hexane (50:50) and then dried under vacuum with a nitrogen sweep to give 1-5 as a white solid.

SCHEME 2

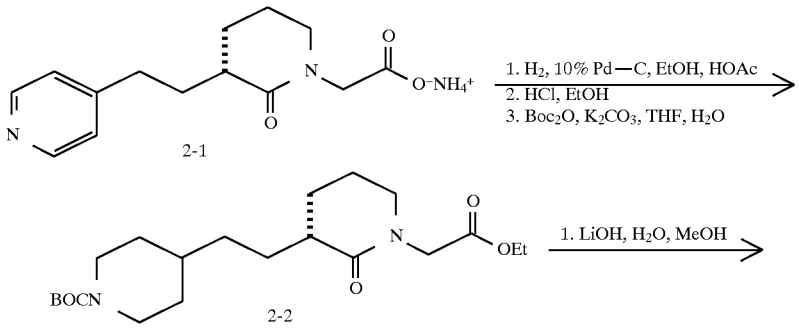

-continued
SCHEME 2

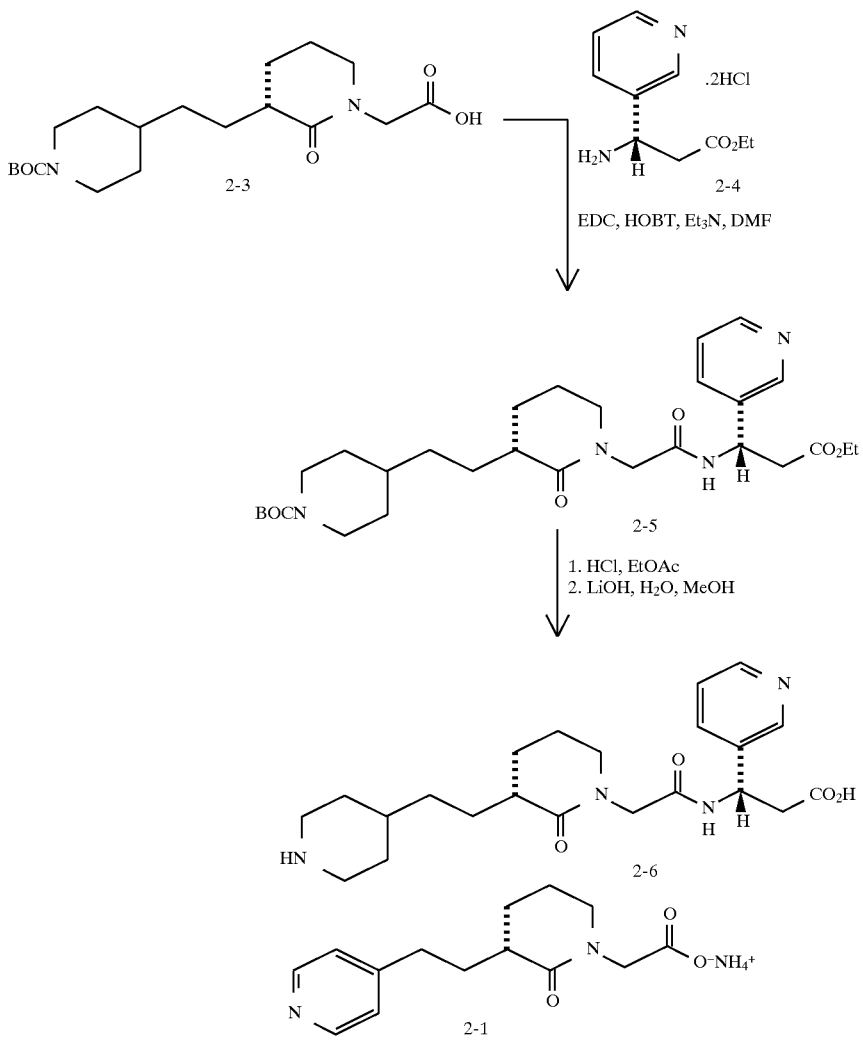

3(R)-[2-(Pyridin-4-yl)ethyl]-2-piperidon-1-ylacetic acid (2-1)

To a solution of 1-5 (6 g, 9.28 mmol) in 100 mL H$_2$O was added conc. NH$_4$OH solution (30 mL) and the mixture stirred for 2 hours. This was then extracted with benzene (4×) and the aqueous layer concentrated in vacuo to give a 2-1 as a viscous oil. This was used as such in the next step.

$^1$H NMR (300 MHz, CD$_3$OD) 67 : 1.6–2.1 (5H, m), 2.17 (1H, m), 2.38 (1H, m), 2.75 (2H, m), 3.38 (2H, m), 3.92 (1H, d), 3.99 (1H, d), 7.33 (2H, d), 8.39 (2H, d).

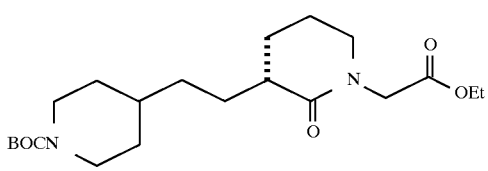

3(R)-[2-(N-Boc-piperidin-4-yl)ethyl]-2-piperidon-1-ylacetic acid ethyl ester (2-2)

A solution of 2-1 (2.55 g, 9.72 mmol) in EtOH (100 mL) and HOAc (6 mL) was purged with argon and then 10% Pd on carbon (250 mg) was added. The mixture was hydrogenated using a Parr apparatus at 57 psi for 16 hours. HPLC analysis indicated only partial hydrogenation so a further 4 mL of HOAc and 200 mg of 10% Pd on carbon was added to the argon purged system. Hydrogenation was continued at 60 psi for 72 hours. After this time, the suspension was filtered through celite and the solvent evaporated in vacuo to give a yellow oil contaminated with HOAc and EtOH which was used as such.

This oil was dissolved in EtOH and treated with HCl gas for 5 minutes until saturated. After stirring at room temperature for 1 hour, the solvent was removed to give the crude ester as a waxy solid which was used without purification in the next step.

This ester was dissolved in THF (25 mL)/H$_2$O (25 mL) and to the solution was added (Boc)$_2$O (2.23 g, 10.2 mmol) and K$_2$CO$_3$ (2.56 g, 18.6 mmol). The mixture was stirred for 16 hours at room temperature then poured into EtOAc and extracted with H$_2$O, brine and dried over MgSO$_4$. The solvent was removed to give an oil which was chromatographed on silica (hexane/EtOAc 1:1) to give 2-2 as an oil.

Rf (silica; hexane/EtOAc 1:1)=0.37 $^1$H NMR (300 MHz, CD$_3$OD) 67 : 0.9–1.1 (2H, m), 1.26 (3H, t), 1.3 (2H, m), 1.4–2.0 (9H, m), 1.44 (9H, s), 2.32 (1H, m), 2.72 (2H, br t), 3.38 (2H, m), 3.95–4.25 (6H, m).

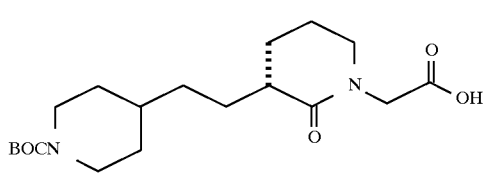

2-3

3(R)-[2-(N-Boc-piperidin-4-yl)ethyl]-2-piperidon-1-ylacetic acid (2-3)

To a solution of the ester 2-2 (2.77 g, 7.0 mmol) in THF (50 mL)/MeOH (50 mL) was added 1N LiOH (28 mL, 28 mmol) and the mixture stirred at room temperature for 16 hours. The solution was neutralised with 1N HCl (pH ~5) and extracted with EtOAc (6×), washed with brine, dried (MgSO$_4$) and evaporated to give a white solid. $^1$H NMR (300 MHz, CD$_3$OD) δ: 0.9–1.15 (2H, m), 1.2–2.05 (11H, m), 1.44 (9H, s), 2.42 (1H, m), 2.72 (2H, br t), 3.4 (2H, m), 3.95–4.15 (4H,m).

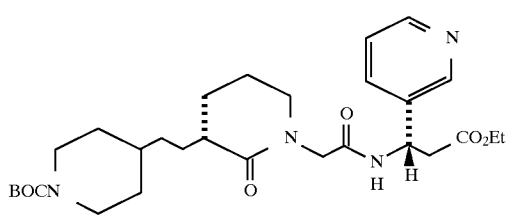

2-5

3(R)-[2-(N-Boc-piperidin-4-yl)ethyl]-2-piperidon-1-ylacetyl-3(S)-(3-pyridyl)-β-alanine ethyl ester (2-5)

A solution of 2-3 (0.368 g, 1 mmol), ethyl 3(S)-(3-pyridyl)-β-aminopropionate dihydrochloride 2-4 (J. Org. Chem., 1993, 58, 7948; 0.267 g, 1 mmol), HOBT (0.149 g, 1.1 mmol) and EDC (0.231 g, 1.2 mmol) in DMF (20 mL) was treated with N-methylmorpholine (0.405 g, 4 mmol). After stirring the resulting solution for 20 hr, the DMF was removed in vacuo and the residue was then partitioned between H$_2$O and EtOAc. The organic layer was washed with a 10% solution of KHSO$_4$, saturated NaHCO$_3$ and brine. Filtration of the dried (Na$_2$SO$_4$) solution and removal of the solvent gave a residue which was purified by chromatography (silica gel eluting with 3% MeOH/CHCl$_3$) to give 2-5. $^1$H NMR (300 MHz, CDCl$_3$) 67 : 0.96–2.0 (25H, m), 2.27–2.40 (1H, m), 2.57–2.76 (2H, br t), 2.80–2.90 (2H, d), 3.34–3.44 (2H, m), 3.93–4.16 (6H, m), 5.36–5.46 (1H, m), 7.22–7.30 (1H, m), 7.60–7.72 (2H, m), 8.52 (1H, d).

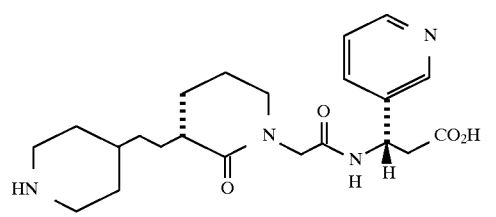

2-6

3(R)-[2-(Piperidin-4-yl)ethyl]-2-piperidon-1-ylacetyl-3 (S)-(3-pyridyl)-β-alanine (2-6)

A solution of 2-5 (0.432 g, 0.793 mmol) in EtOAc (20 mL) was cooled to −20° C. and HCl (gas) was bubbled through for 10 minutes. The solution was allowed to warm to 0° C. and stirred for 1 hr. The solvent and excess HCl was removed in vacuo to give the deprotected piperidine as the HCl salt.

A solution of the piperidine (0.215 g, 0.416 mmol) in THF/MeOH/H$_2$O (1/1/1; 20 mL) was treated with LiOH.H$_2$O (0.087 g, 2.08 mmol) and stirred for 24 hrs. The solvent was removed in vacuo and the residue was purified by preparative HPLC (H$_2$O, CH$_3$CN with 0.1% TFA) to give 2-6 as the TFA salt. $^1$H NMR (300 MHz, CD$_3$OD) 67: 1.22–2.02 (14H, m), 2.25–2.40 (1H, m), 2.85–3.08 (4H, m), 3.26–3.50 (3H, m), 3.94–4.14 (2H, q), 5.38–5.49 (1H, t), 7.97–8.06 (1H, m), 8.55–8.64 (1H, d), 8.74–8.0 (1H, d), 8.90 (1H, s).

Therapeutic Treatment

Compounds of the invention may be administered to patients where inhibition of human or mammalian platelet aggregation or adhesion is desired.

Compounds of the invention are useful in inhibiting platelet aggregation and thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

EXAMPLE 3

Tablet Preparation

Tablets containing 25.0, 50.0, and 100.0 mg., respectively, of the active drug 3(R)-[2-(Piperidin-4-yl)ethyl]-2-piperidon-1-ylacetyl-3(S)-(3-pyridyl)-β-alanine are prepared as illustrated below:

| TABLE FOR DOSES CONTAINING FROM 25–100 MG OF THE ACTIVE COMPOUND | | | |
|---|---|---|---|
| | Amount-mg | | |
| Active Drug | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active drug, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 4

Intravenous formulations

An intravenous dosage form of the above-indicated active drug is prepared as follows:

| Active Drug | 0.5–10.0 mg |
|---|---|
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active drug is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

EXAMPLE 5

Intravenous formulation

A pharmaceutical composition was prepared at room temperature using 3(R)-[2-(Piperidin-4-yl)ethyl]-2- piperidon-1-ylacetyl-3 (S)-(3-pyridyl)-β-alanine, a citrate buffer, and sodium chloride, to obtain a concentration of of 0.25 mg/ml, 800 grams of water was introduced into a standard pharmaceutical mixing vessel. 0.25 grams of 3(R)-[2-(Piperidin-4-yl)ethyl]-2-piperidon-1-ylacetyl-3(S)-(3-pyridyl)-β-alanine was dissolved in the water. 2.7 grams sodium citrate and 0.16 grams citric acid were added to obtain a finished citrate concentration of 10 mM. 8 grams of sodium chloride was added. 200 grams of water was then added to achieve the desired final concentrations of ingredients. The resulting aqueous formulation had the following concentrations:

| Ingredient | Amount |
| --- | --- |
| 3(R)-[2-(Piperidin-4-yl)ethyl]-2-piperidon-1-ylacetyl-3(S)-(3-pyridyl)-β-alanine | 0.25 mg/ml |
| citrate buffer | 10 mM |
| sodium chloride | 8 mg/ml |

The finished concentrated formulation is stored in a standard USP Type I borosilicate glass container at 30–40 degrees C. Prior to compound administration, the concentrated formulation is diluted in a 4:1 ratio resulting in a finished concentration of 0.05 mg/ml and transferred to an infusion bag.

What is claimed is:

1. A compound which is 3(R)-[2-(Piperidin-4-yl)ethyl]-2-piperidon-1-ylacetyl-3(S)-(3-pyridyl)-β-alanine or a pharmaceutically acceptable salt thereof.

2. A compound of claim 1 which is 3(R)-[2-(Piperidin-4-yl)ethyl]-2-piperidon-1-ylacetyl-3(S)-(3-pyridyl)-β-alanine.

3. A pharmaceutical composition comprising a therapeutically effective amount of a compound of claim 1 and a pharmaceutically acceptable carrier.

4. A method for inhibiting the aggregation of blood platelets in a mammal, comprising treating the mammal in need thereof with a platelet aggregation inhibting amount of a composition of claim 3.

5. A method for inhibiting the aggregation of blood platelets in a mammal, by blocking fibrinogen from acting at its receptor site, comprising treating the mammal in need thereof with a fibrinogen receptor blocking amount of a composition of claim 3.

* * * * *